United States Patent [19]
Preen et al.

[11] Patent Number: 5,449,347
[45] Date of Patent: Sep. 12, 1995

[54] PATIENT TRANSPORT, PLURAL POWER SOURCE SUCTION APPARATUS

[75] Inventors: Philip J. Preen, Universal City; Thomas Waters, Sheppard AFB, both of Tex.

[73] Assignee: The United States of America as represented by the Secretary of the Air Force, Washington, D.C.

[21] Appl. No.: 273,443

[22] Filed: Jul. 5, 1994

[51] Int. Cl.⁶ .............................................. A61M 1/00
[52] U.S. Cl. ..................................... 604/118; 604/317
[58] Field of Search ............... 604/317, 318, 118, 119; 128/760, 761, 765

[56] References Cited

U.S. PATENT DOCUMENTS

| | | | |
|---|---|---|---|
| 4,631,061 | 12/1986 | Martin | 604/318 |
| 4,857,063 | 8/1989 | Glenn | 604/317 |
| 4,976,694 | 12/1990 | Schreibman | 604/140 |
| 5,009,641 | 4/1991 | Gorton | 604/131 |
| 5,242,407 | 9/1993 | Struble et al. | 604/151 |
| 5,244,463 | 9/1993 | Cordner, Jr. et al. | 604/131 |

FOREIGN PATENT DOCUMENTS

| | | | |
|---|---|---|---|
| 4193263 | 7/1992 | Japan | 128/760 |

*Primary Examiner*—Jerome L. Kruter
*Attorney, Agent, or Firm*—Gerald B. Hollins; Thomas L. Kundert

[57] ABSTRACT

A portable, patient assignable, medical suction apparatus usable especially in the medical evacuation field. The suction apparatus includes self contained battery energy sourcing in addition to capability of operation and battery charging from a variety of alternating and direct current energy sources as are commonly available in transportation vehicles and ground based medical facilities. The disclosed apparatus includes provisions for suction canister usage, electromagnetic interference reduction, mounting on an existing aircraft stanchion and shelf and hand carriage to a patient's bedside. Military usage and possible civilian usage are also disclosed.

16 Claims, 3 Drawing Sheets

PATIENT TRANSPORT, PLURAL POWER SOURCE SUCTION APPARATUS

RIGHTS OF THE GOVERNMENT

The invention described herein may be manufactured and used by or for the Government of the United States for all governmental purposes without the payment of any royalty.

BACKGROUND OF THE INVENTION

This invention relates to the field of medical suction apparatus.

Continuing improvement in the battle area medical care available to U.S. military personnel has been noted in the lay media and is a matter of considerable pride to the U.S. military. One need only compare the practice of dispatching military wounded by helicopter to nearby field hospital facilities as used in the Southeast Asian and recent Middle East conflicts with the hours of delay that was frequent in World War II and the days of delay that ensued in the World War I and U.S. Civil War era to appreciate the increased chances of survival and quality of life maintenance available to a present day wounded military person. These improvements have also been carried into everyday life in the form of helicopter equipped trauma centers located in most major cities of the United States.

This continuing degree of medical care improvement is of course based on increased medical knowledge and immensely improved treatment options such as more effective drug therapy, but in addition is based on an increased availability of basic medical equipment—equipment that operates well under adverse conditions. The present invention is concerned with one example of this improved equipment—a portable and individual patient assignable suction apparatus. Equipment of this type is often needed for removing patient jeopardizing fluid accumulations from a chest cavity wound or a breathing passage-way for example. The present invention apparatus is therefore arranged to be compatible with most environments expected during a military medical treatment and evacuation and most notably is usable during the several phases of transportation that a wounded military person may experience before reaching a permanent or long term care facility where a basic requirement such as suction is available as an "in the wall" utility.

The apparatus of the present invention can for example be employed in a battlefield situation by a medical corpsman and the same apparatus used to accompany the wounded person on an air evacuation helicopter to a local field hospital. The apparatus may continue in its assignment to a particular person during transport from the field hospital to a well behind the lines zonal medical facility and continue even further with this assigned patient during transportation from the zonal hospital to a U.S. mainland medical facility in a multi engine large transport aircraft. The C-130 and C-141 aircraft presently used by the U.S. Air Force for such long distance medical transportation are particular candidates for use of apparatus according to the present invention since continuous suction capability is not provided in these aircraft and medical transportation flights of four to twelve hours duration are commonly encountered with such aircraft.

The energy sources available for operating medical equipment such as the present invention suction apparatus may of course vary from zero in a battlefield situation to the low voltage DC systems available in ground vehicle and smaller aircraft and older aircraft to the 400 Hertz three phase systems used on more modern aircraft. Ultimately the 115 volt 60 Hertz or 230 volt 50 Hertz energy that is commonly available in U.S. or European hospital facilities is available for operating such equipment. In the present invention apparatus accompaniment of a patient through environments having several or all of these energy sources is desirable.

In the initial battlefield use of an assigned suction apparatus, self contained energy sourcing is of course desirable; this self contained energy sourcing is also useful in stretcher and litter transportation situations and in patient staging areas. At the other extreme for such equipment—during the four to twelve hour flight over water, the ability to use available aircraft energy to maintain uninterrupted operation of this same suction equipment is also of significant value.

The U.S. Patent Art illustrates several examples of medical apparatus that is of general background interest with respect to the present invention. Included in this patent art is the U.S. Pat. No. 4,976,694 of G. Schreibman which is concerned with an apparatus and method for preventing infection. In the Schreibman invention a battery operated vacuum pump is used for the purpose of removing contaminated tissue and fluids from a localized skin wound immediately after contamination has occurred. The Schreibman apparatus employs a biopsy punch a tourniquet and other implements as may be helpful in the immediate decontamination of a wound. The disclosed apparatus is however not suited for the immediate and long term uses of a patient and for use in a transportation situation.

The patent art of general interest also includes U.S. Pat. No. 5,009,641 of L. A. Gorton an apparatus in which a patient is provided with means of self administering analgesia or pain medication in response to his/her request. Since the Groton apparatus is concerned with medication administration and with patient initiated action, a ready distinction from the present invention is apparent.

The Patent Art of general background interest, also includes U.S. Pat. No. 5,242,407 of K. R. Struble et al which discloses a medication infusion pump for administering intravenous fluids to a patient. The absence of a vacuum system or multiple energy sourcing and other present invention capabilities are submitted to distinguish the present invention from the Struble et al invention.

The U.S. Pat. No. 5,244,463 of E. T. Cordner, Jr. et al also discloses a medication administering infusion pump.

SUMMARY OF THE INVENTION

The present invention concerns a patient assignable medical suction apparatus usable for short term and long term care of a patient needing collected fluid evacuation—especially during a plurality of transportation related medical situations. The suction apparatus is provided with several conveniences including suction level control and monitoring, internal or a plurality of external energy sources, operating status indications, and expected environment mounting and carrying capabilities. The apparatus also provides for continuous or intermittent operating cycles, the use of suction canister equipment and is especially suited for service use during long military medical evacuation flights.

It is an object of the present invention therefore to provide a multiple energy source suction apparatus for medical usage.

It is another object of the invention to provide a patient assignable medical suction apparatus.

It is another object of the invention to provide a medical suction apparatus having both continuous and predetermined intermittent cycle operating capabilities.

It is another object of the invention to provide a medical suction apparatus of controllable suction capability.

It is another object of the invention to provide a medical suction apparatus having internal and plural external energy supply capabilities.

It is another object of the invention to provide a medical suction apparatus that is limited in radio frequency interference (RFI) generation characteristics.

Additional objects and features of the invention will be understood from the following description in claims and the accompanying drawings.

These and other objects of the invention are achieved by: Individual patient assignable portable medical suction generating apparatus comprising the combination of:

a low voltage direct current electrical energy operable suction pump member received in a hand carriable and patent litter apparatus mountable housing member;

a manually adjustable suction pressure controlling member shunt connected to a suction conduit member joining a suction inlet port of said suction pump member and a suction communicating port of said apparatus;

a rechargeable electrical battery member physically received within said housing member and having a nominal low voltage terminal potential that is compatible with said suction pump member;

first electrical input port means for receiving externally sourced direct current electrical energy into said apparatus;

first means for converting direct current electrical energy received at said first electrical input port means to battery charging direct current energy and suction pump operating direct current energy of said battery member nominal low terminal voltage level;

second electrical input port means for receiving externally sourced alternating current electrical energy of predetermined differing voltage level and differing alternation frequency characteristics into said apparatus;

second means for converting alternating current electrical energy received at said second input port means to battery charging direct current electrical energy and suction pump operating direct current electrical energy of said battery member nominal low terminal voltage level;

switching means for selecting between electrical energy input from said electrical battery number, said first input port means and said second input port means in response to manual and predetermined automatic selection criteria for energizing said suction pump member;

electronic timing circuit means responsive to a manual election input for operating said suction pump member in either a predetermined cycle of energized and non energized operating events or a continuously energized operating event.

DETAILED DESCRIPTION

Figure 1:
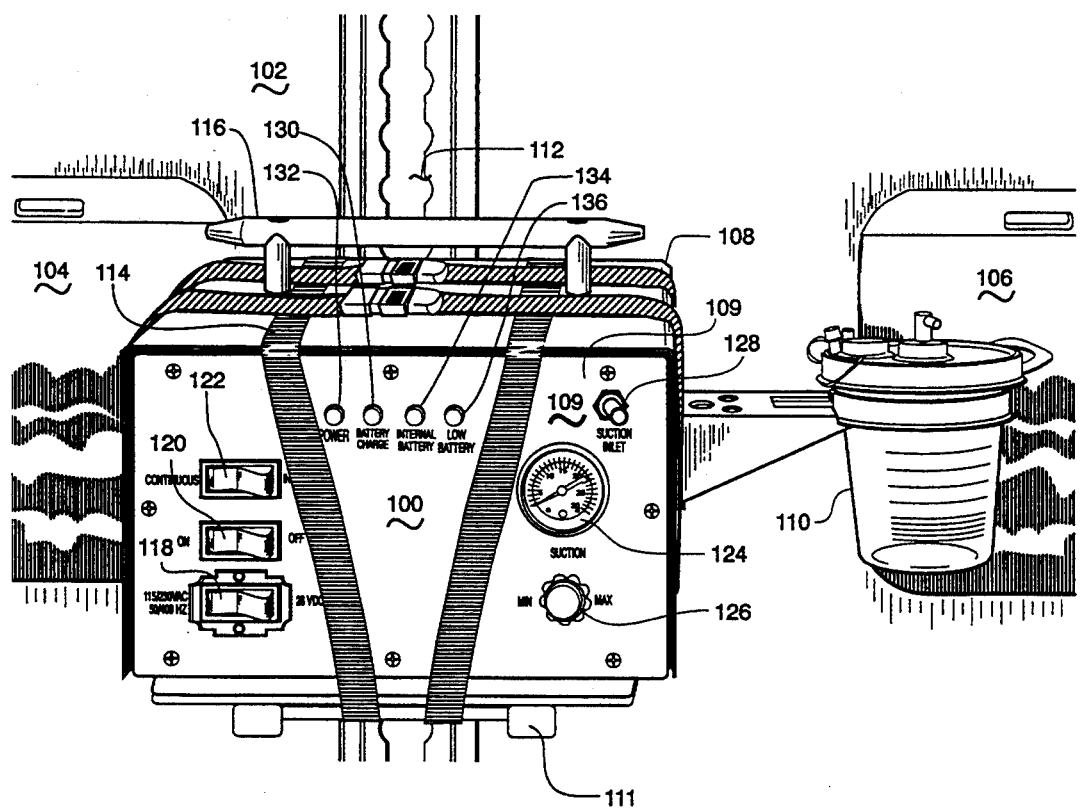
FIG. 1 shows an overall view of a medical suction apparatus according to the invention with the apparatus mounted in an aircraft.

FIG. 1 in the drawing shows a medical suction generating apparatus according to the present invention in one of its intended environments, a medical transportation arranged military cargo aircraft.

In the FIG. 1 drawing the medical suction apparatus 100 is shown to be located adjacent an interior wall 102 of a host aircraft and disposed between two window apertures, 104 and 106, of this aircraft. The suction generating apparatus 100 is shown in FIG. 1 to be mounted on a upstanding post 112 which is part of a "Waters shelf" apparatus that is commonly used in military medical aircraft. The shelf portion of this apparatus is visible at 111 below the housing 108. The suction generating apparatus is secured to this shelf by way of a series of tie down straps which are indicated generally at 114 in FIG. 1. The tie down straps 114 are mated with a handle assembly 116 that is also provided with strap receiving apertures.

The suction apparatus 100 includes a suction generating pump assembly and related components, located within the housing 108, and a canister receptacle portion 110 which is removably mounted on either side of the housing 108. The housing 108 of the FIG. 1 suction generating apparatus 100 includes a front panel portion 109 which mounts several components used in controlling and monitoring operation of the apparatus. Included in these front panel mounted components is a group of three electrical switches 118, 120, and 122 which respectively select the alternating or direct current input energy capabilities of the apparatus, the ON or OFF operating status of the apparatus and the continuous or intermittent operating cycle of the suction generating apparatus.

Also received on the front panel 109 is a suction monitoring gage 124, a suction control knob member 126, and a suction inlet port 128. At the top most and center portion of the panel 109 are located a series of four indicator lamps, which may be of the light emitting diode type for example, as are represented at 130, 132, 134, and 136. These indicator lamps are arranged to indicate power on, battery charging, internal battery operation and low internal battery condition respectively.

Although not clearly visible in the FIG. 1 drawing, the power selection switch 118 is provided with two positions, one, the illustrated left-most switch position, for selecting 115/230 volts alternating current energization of the FIG. 1 apparatus and the other for selection of 28 volt DC aircraft power for energizing the FIG. 1 apparatus. The ON and OFF switch 120 is shown in the left most or ON position in the FIG. 1 view and the continuous intermittent/switch 122 is shown to be in the right most or intermittent operation position. The suction monitor gage, 124 is preferably provided with scaled readings between zero and seven hundred sixty millimeters of mercury column or alternately between zero and 30 inches of mercury column, the intended suction range of the FIG. 1 apparatus.

Figure 2:
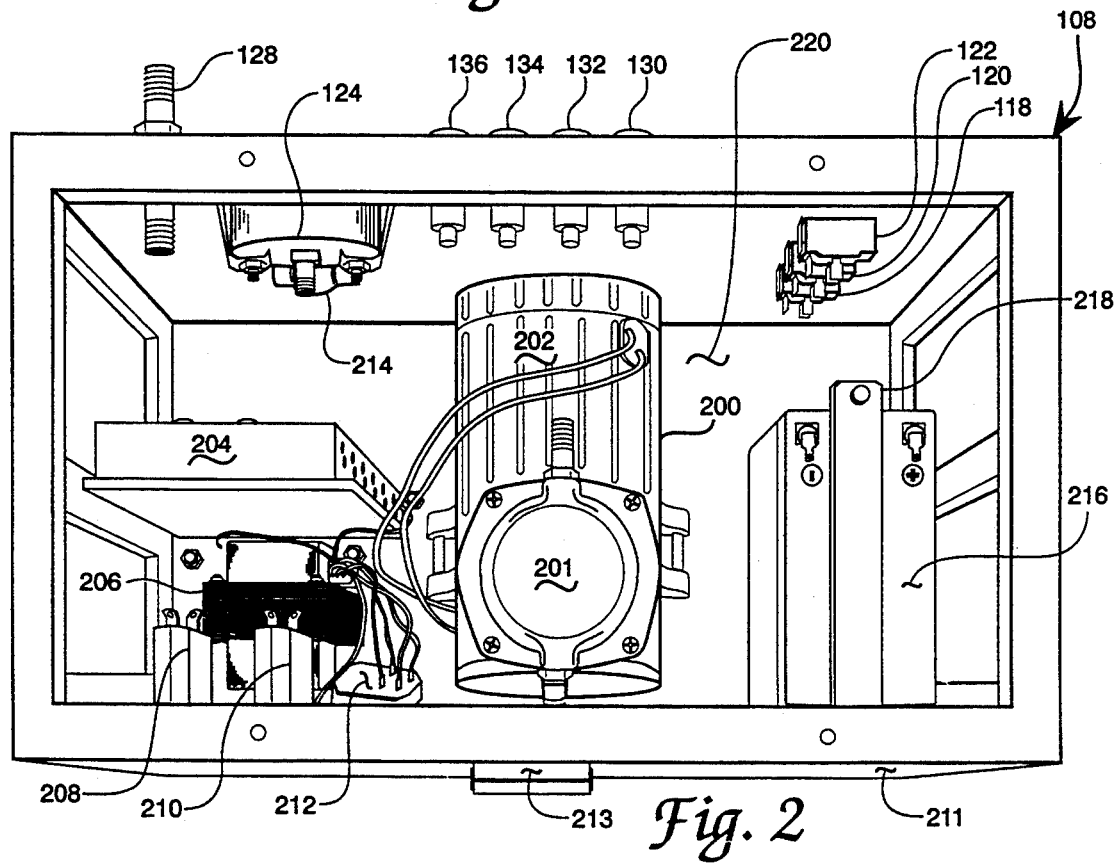
FIG. 2 shows an internal component view of the FIG. 1 apparatus.

FIG. 2 in the drawings shows a top-panel-removed internal view of the FIG. 1 suction generating apparatus, a view wherein the internal tubing and wiring of the apparatus is also removed for clearer identification of the major internal components. Numbers from the FIG. 1 drawing are repeated as appropriate for the FIG. 2 illustrated components. In addition to these FIG. 1 identified components, there appears in FIG. 2 a suction generating pump assembly 200 which includes a 12 volt direct current motor portion 202 and a vacuum generating portion 201. Also appearing in the FIG. 2 drawing is a switching-type DC to DC converter assembly, with its heat sinking elements indicated at 204, a step-down transformer 206, and full a wave bridge rectifier 212—components of an alternating current power supply apparatus. A pair of input current limiting circuit breaker members, 208 and 210 are also shown in FIG. 2; these circuit breakers 208 and 210 are actually mounted on the rear panel 211 of the FIG. 1 and FIG. 2 apparatus and have operating push button controls which extend through this panel. Additionally received on the rear panel 211, but not shown in the FIG. 2 drawing is an input receptacle for a 28 volt DC connecting cord, an input receptacle for an alternating current power cord and a selection switch enabling use of either 115 volts or 230 volts alternating current energy input. The AC and DC circuit breakers 208 and 210 may have a current ratings of 1 and 8 amperes respectively. Also shown on the back panel 211 of the FIG. 2 apparatus is the mechanical connector member 213 by which the apparatus was shown to engage the upstanding post 112 in FIG. 1.

Additional components appearing in the FIG. 2 top view drawing are the suction control valve 214, the rechargeable internal battery 216, and its hold-down strap assembly 218. Although not shown in the FIG. 2 drawing, the battery 216 is preferably received in a close fitting rectangular cup member that is mounted on the floor 220 of the housing 108.

Figure 3:
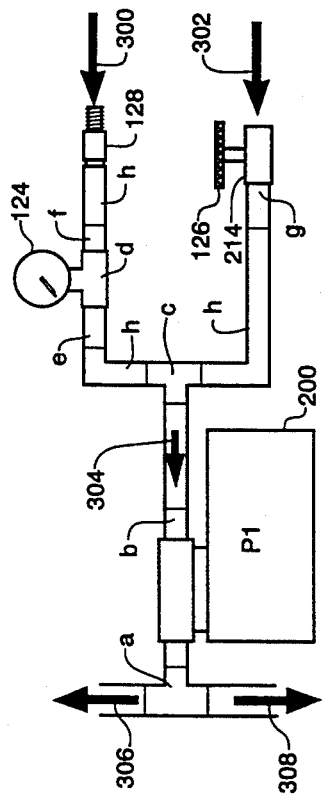
FIG. 3 shows a mechanical schematic of the FIG. 1 and FIG. 2 medical suction apparatus.

FIG. 3 in the drawings shows a suction system mechanical schematic for the FIG. 1 and FIG. 2 apparatus. In the FIG. 3 drawing, several of the components are identified with the identification numbers used in FIG. 1 and FIG. 2 and several additional of the components are provided with letter or letter and number identifications which correspond to the identifications appearing in the Table 1 Mechanical Parts listing which appears below.

TABLE I

| MECHANICAL PARTS | | |
|---|---|---|
| Identity | Value, Identity | Description |
| a | L-06451-21 | Male pipe adapter, Tee ¼" NPT; tubing ID ⅜" |
| b | L-06450-40 | Male pipe adapter ¼" NPT; tubing ID ¼" |
| c | L-06452-40 | Male branch, Tee ¼" NPT Tubing ID; ¼" |
| d | #2FTP | FTP Female Tee, Brass ¼" NPT |
| e,f,g | L-06450-12 | Male pipe adapter ¼" NPT; tubing ID ⅛" |
| h | | ¼" Plastic tubing |

TABLE I-continued

| MECHANICAL PARTS | | |
|---|---|---|
| Identity | Value, Identity | Description |
| Suction Inlet Valve | | Bellows sealed valve, Brass ¼" NPT inlet & outlet |
| Suction Adjust Valve | | Needle valve, Brass ¼" NPT female |
| Vacuum Gauge | | 0-30 in Hg vacuum gauge ¼" NPT, 2.5" dia, panel mount |

Additional information concerning the FIG. 3 mechanical schematic diagram of the FIG. 1-2 apparatus is to be found in Table 2 below herein. In this Table, the schematic symbols appearing with each of the parts in the FIG. 3 diagram is related to a part value or identity and a description of the part and its function is provided in concise narrative form.

TABLE 2. MECHANICAL SCHEMATIC DESCRIPTION

Air is drawn through the suction inlet port by the suction pump.

The suction adjust valve utilizes bleed air to reduce the level of vacuum at the suction inlet port.

The vacuum gauge is positioned in line and will indicate the suction level present at the suction inlet port.

The exhaust from the motor is run through a T connector.

One T outlet tube supplies cooling air to the circuit board components and the other outlet tube supplies cooling air to T1 and FWB.

Tee exhaust flow creates a positive air pressure inside of the housing forcing warm air out.

The side mounted disposable suction canister brackets are utilized by sliding the suction canister holder into a corresponding side bracket. Only one suction canister can be used at a given time, but the availability of two holders prevents having to move the suction apparatus. The medical attendant can simply attach the suction tubing to the nearest canister in relation to the patient.

Figure 4:
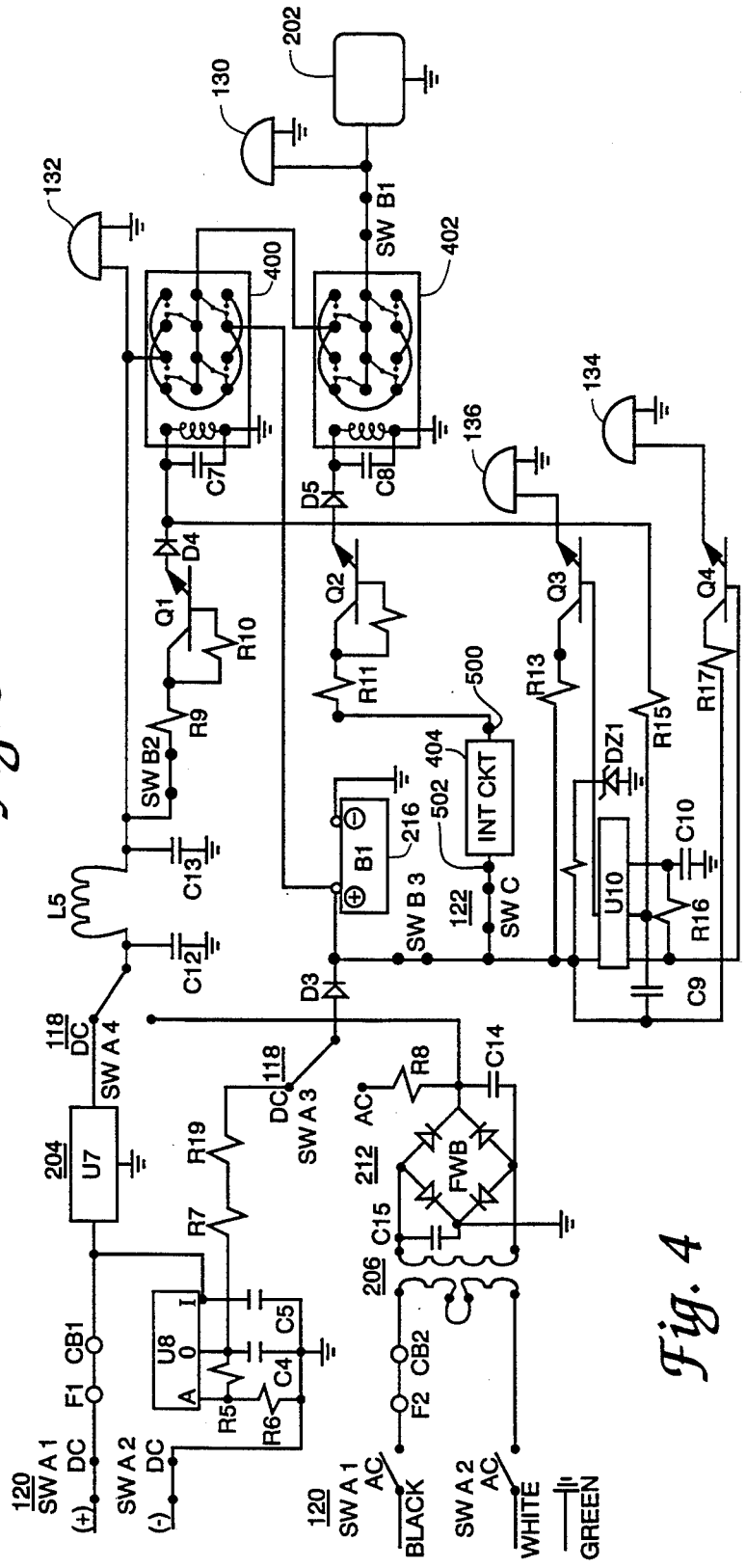
FIG. 4 shows an electrical schematic of the FIG. 1–FIG. 3 medical suction apparatus.
Figure 5:
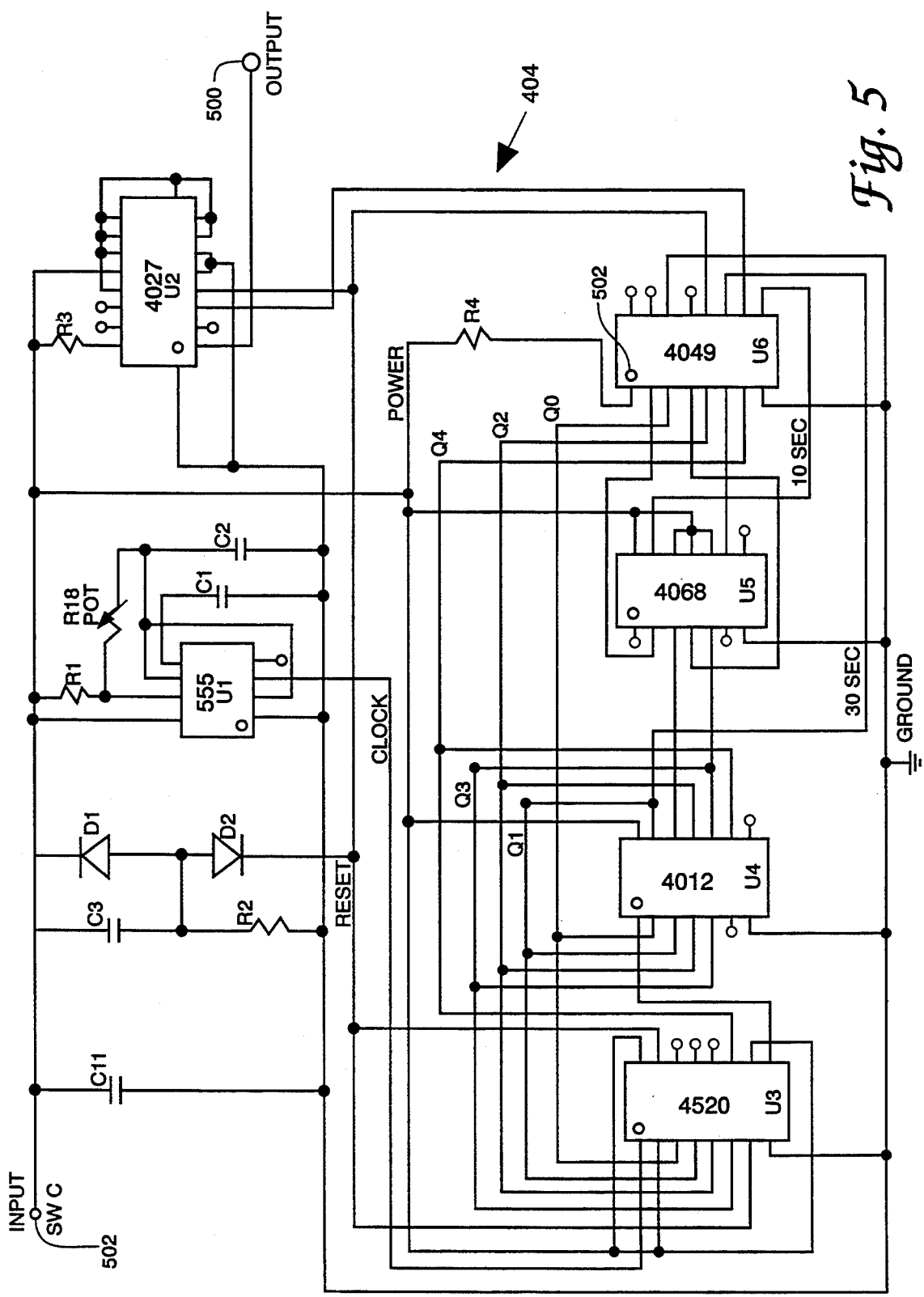
FIG. 5 shows an electrical schematic of a subsystem in the FIG. 4 electrical schematic, an intermittent operation controlling subsystem.

FIG. 4 in the drawing shows an electrical schematic diagram of the FIGS. 1-3 suction apparatus and includes most of the components illustrated in FIGS. 1-3 along with their previously used identification numbers. Additional components appearing in FIG. 4 include the two DC operated multiple poled relays 400 and 402 and the block 404 which is used to identify the intermittent operation circuitry portion of the apparatus which is more fully disclosed in FIG. 5 of the drawings. The step down transformer 206 is shown in the FIG. 4 drawings to be provided with a dual winding primary which is represented to be connected in its highest voltage or 230 volts input configuration. The upper and lower portions of this primary winding may of course be connected in a parallel configuration for 115 volt input energy as is known in the electrical art. Table 3 which appears below provides a listing and identification of the parts appearing in the FIG. 4 electrical schematic.

TABLE 3

| ELECTRONIC PARTS LIST | | |
|---|---|---|
| Schematic Symbol | Value, Identity | Description |
| U1 | SK3564 | 555 TIMER |
| U2 | 4027BMJ | DUAL J-K FLIP-FLOP |
| U3 | 4520BCL | DUAL UP COUNTERS |
| U4 | 4012UBCL | DUAL 4-INPUT "NAND" GATE |
| U5 | 4068BC | 8-INPUT "NAND" GATE |

TABLE 3-continued
ELECTRONIC PARTS LIST

| Schematic Symbol | Value, Identity | Description |
|---|---|---|
| U6 | 4049U | HEX BUFFERS |
| U7 | KZ432 | 12 VOLT DC-DC CONVERTER |
| U8 | LM317T | VOLTAGE REGULATOR |
| U10 | LM358 | DUAL OP-AMP (8-PIN) |
| L5 | 150 mH | INDUCTOR RFI 1 IN DIAMETER |
| R1 | 620KΩ | .5 W; RESISTOR |
| R2 | 13KΩ | .5 W; RESISTOR |
| R3, R4 | 3300KΩ | .5 W; RESISTOR |
| R5 | 240Ω | .5 W; RESISTOR |
| R6 | 3KΩ | .5 W; RESISTOR |
| R7 | 1.5Ω | .5 W; RESISTOR |
| R8 | 3Ω | 50 W; RESISTOR |
| R9 | 22Ω | .5 W; RESISTOR |
| R10, R12 | 110Ω | .5 W; RESISTOR |
| R11 | 4KΩ | .5 W; RESISTOR |
| R13, R17 | 22Ω | .5 W; RESISTOR |
| R14 | 75Ω | 5 W; RESISTOR |
| R15, R16 | 3300Ω | .5 W; RESISTOR |
| R18 | 100KΩ | POT; RESISTOR |
| R19 | 1Ω | 1 W; RESISTOR |
| C1 | .1 μF | 15 V PLASTIC; CAPACITOR |
| C2 | 2 μF | 15 V PLASTIC; CAPACITOR |
| C3 | 47 μF | 15 V; CAPACITOR |
| C4 | 1 μF | 30 V PLASTIC; CAPACITOR |
| C5 | .1 μF | 30 V PLASTIC; CAPACITOR |
| C6, C12, C13 | 4700 μF | 25 V ELECTROLYTIC; CAPACITOR |
| C7, C8, C10 | 1 μF | 15 V PLASTIC; CAPACITOR |
| C9 | 1 μF | 15 V PLASTIC; CAPACITOR |
| C11 | 1 μF | 15 V PLASTIC; CAPACITOR |
| C13, C14, C15 | .1 pF | 100 V PLASTIC; CAPACITOR |
| D1, D2, D4, D5 | 1N4002 | 1 A DIODE |
| D3 | K8226 | 3 A DIODE |
| DZ1 | 9.6 V | 1 A ZENER DIODE |
| Q1-Q4 | 2N2222 | TRANSISTOR |
| CB2-CB1 (208, 210) | W23-X1A1G-{1,8} | 1 & 8 AMP CIRCUIT BREAKERS |
| F1-F2 | MDV (1,8) 250 V | 1 AMP, 5 AMP SLOW BLOW FUSES |
| B1 | PS1270 | 12 VOLT BATTERY |
| RELAYS (400, 402) | R10-E1-X4-V185 | 4PDT, 12 VDC, P & B |
| FWB | SK3988 | 8 A FULL WAVE BRIDGE |
| T1 | P-6378 | 115-230 VAC/50-400 Hz TRANSFORMER |
| L1-L4 | JKL 330 | 12 VDC LED |
| SWA | TIIL51-1C-BL-FW/BLK | 4 Pole 2 Throw ROCKER SWITCH |
| SWB | TIHK51-1C-BL-FW/BLK | 4 Pole 1 Throw ROCKER SWITCH |
| SWC | TIHK51-1C-BL-FW/BLK | 4 Pole 1 Throw ROCKER SWITCH |
| SWD | V-SERIES | 230/115 V SLIDE SWITCH |
| VACUUM PUMP | MODD107CDC20 | 12 VDC, 1/10 HP, 8 A, DIAPHRAGM, THOMAS INDUSTRIES |

In addition to the part listing and identification of Table 3 above, a description of the operation of the FIG. 4 of the electrical apparatus in outline form is provided in Table 3 herein. In this Table 4 outline description part identities are provided along with a brief recitation of the part function in the FIG. 4 diagram.

TABLE 4, OPERATION OF THE FIG. 4 CIRCUIT

A. For Switch A, in DC position:

In this position the AC components are isolated from DC input power. A DC cord is plugged into the back of the apparatus.

Fuse F1 and Circuit Breaker CB1 protect the components from internal shorts or motor seizure.

U7, 12 Volt DC to DC converter, converts the 28 VDC input into regulated 12 VDC power which is used to operate the pump. U8, 317T Voltage Regulator, converts 28 DC input into a regulated 16 VDC to charge battery B1 and operate the circuitry. The output is also regulated to limit the charge current.

B. The following applies: in either the AC or DC position.

Diode D3 isolates the AC or DC circuitry from the internal battery. Inductor L5, capacitors C12, and C13, comprise a low-pass EMI filter. With switch B in the ON position, power will be present at resistor R9, transistor Q1 and resistor R10.

When Q1 is biased it will turn ON and energize Relay A. This will hold the contacts open and 12 VDC will be applied to Relay B.

All normally open contacts are connected in parallel in each relay, also all normally closed contacts.

In the event the voltage at Q1 falls below 12 VDC and switch B is in the ON position, Q1 will turn OFF. The contacts of Relay A will close and 12 volt internal battery power will be applied to the suction pump.

This allows automatic switch-over from line power to battery power and uninterrupted service to the patient.

Diodes D4 and D5 isolate the FIG. 4 circuit from Relay A and Relay B inductive voltage spikes.

LED L2, Battery Charge indicator, will illuminate when external power is applied.

The following description applies for operation on internal battery. When switch B is in the ON position and switch C is in the intermittent position, the intermittent circuitry 404 is activated.

When the output of circuitry 404 is high, resistors R11 and R12 bias transistor Q2 ON and energize Relay B. This holds the contacts open and the output to the pump is zero.

When the output of 404 is low, Relay B is turned OFF, the contacts are closed, and the power supplied by Relay A is used to power the pump. Relay A and Relay B operate in this manner to save energy.

When line power is present Relay A remains energized and this power is applied to Relay B which is normally closed.

The only time pump operating power is required from the battery is in the intermittent mode; 40 seconds of each minute.

LED L1, Power indicator, will illuminate when power is supplied to operate the pump.

With switch B, in the ON position, power is applied to U10, 747 dual Op-Amp.

One Op-Amp is utilized as a comparator using resistor R14 and diode DZ1. It monitors the power to the chip and compares it to the 9.6 volt reference voltage provided by zener diode DZ1.

If the line voltage drops below this value, an analog signal will bias transistor Q3, sending power to LED L4 (low battery). Resistor R13 controls the current flowing through Q3 to L4. When the line voltage is above 9.6 volts, Q3 will be turned OFF and L4 will not light.

The apparatus will continue to operate without the internal battery in place and the low battery will remain lighted as a reminder that a battery is not available for use.

The other Op-Amp is also used as a comparator. Both inputs to the Op-Amp are referencing line power and battery power simultaneously.

Resistors R15 and R16 provide an equal reference for both sources. Capacitors C9 and C10 provide railing of the corresponding signal high or low in the event one of the references changes. With both signals present a zero analog output is sent to transistor Q4 and LED L3 will not light. With only the battery signal present an analog signal is sent, Q4 is biased, and L3 lights.

Resistor R17 controls the current flowing through Q4 to L3. The L3 (internal battery) indicator informs the operator that the apparatus is operating on internal battery power.

C. Switch A, VAC position:

In this position the DC components are isolated from the AC power. The AC power cord is connected to an AC socket on the back of the apparatus. Switch D on the back panel, allows the apparatus to be operated in the 115 VAC or 230 VAC position.

Fuse F2 and Circuit Breaker CB2 protect the apparatus from internal shorts or motor seizure.

Incoming VAC line power is passed through stepdown transformer T1. The voltage power is stepped down from the line power to 12 VAC.

The full wave bridge rectifier (FWB), rectifies the AC voltage to DC voltage. Capacitors C14 and C15 decrease RFI noise Resistor R8 limits the charging current of the internal battery. In this unregulated configuration there is no circuitry to keep the voltage and current output at switch A 4, AC, constant.

When the unit is not operating, FWB has a voltage output of 16 V at 1 A. The voltage drop across D3, typically 0.7 volts, provides 15 volts to bias the battery. (Gel cell type batteries maintain a deep charge at a high voltage). When the unit is operating, FWB has a voltage output of 13 volts at 6.5 A. The voltage drop across R8 is minimal to allow maximum voltage output to the internal battery.

This voltage potential insures the battery charges at all times when the unit is operating on a VAC power source and is limited to a 1 amp current flow. Switch A 3 and switch A 4 are in the AC configuration. The operation at this point is the same as switch A 3 and switch A 4 switched to the DC position. See B above for a full description.

D. The intermittent circuitry represented at 404 in FIG. 4 is shown in schematic form in FIG. 5 of the drawings. As indicated in this drawing, this circuitry includes six standard integrated circuit chips which are connected in a time delay generating arrangement. The standard electronic industry identification of the circuit chips used in the FIG. 5 intermittent timing circuit is provided in Table 3 above. The Pin numbering of these circuit chips follows the conventional arrangement wherein Pin 1 is identified with a white circle inside the circuit identifying rectangle and the ensuing pins proceed downward or to the right and upward or to the left for the opposite side disposed pins. The discrete components appearing in the FIG. 5 circuit are also identified in Table 3. The time modulated output of the FIG. 5 circuit appears at 500 and the input at 502; these nodes are identified in the FIG. 4 schematic. An outline description of the function of the components in the FIG. 5 circuit appears in Table 4 below herein.

TABLE 4 THE INTERMITTENT TIMING CIRCUIT, 404

The intermittent circuitry sends a low analog signal for 10 seconds when switch C is set in the Intermittent position and switch A is in the ON position. This activates the circuitry to operate the pump.

A high analog signal is then applied for 20 seconds which correspondingly stops the pump.

This cycle is repeated until either switch C is set in the Continuous position or switch B is set in the Off position.

If the unit is turned ON in the intermittent configuration it will start its cycle by operating for the initial 10 seconds.

Power is supplied to the intermittent circuitry when switch C is in the intermittent position.

Capacitor C11, buffers the power to the board when switch C closes. Once power is applied a 0.5 sec delay ensues as capacitor C3 charges according to a time constant determined by resistor R2. While capacitor C3 charges, it applies a high signal to the Dual Up Counter U3 which resets the chip and insures a zero analog output for initiation of the sequence. U2, a Dual J-K Flip Flop, sends a low signal to the output node 500. Diodes D1 and D2 isolate the delay portion of the circuit after t=0.5 seconds. U1, a 555 timer, is configured to send out a high analog signal at one second intervals. This signal establishes the counting mechanism for the CMOS logic.

U3 receives the timer signal and initiates a binary counting sequence. U4, Dual 4-Input "Nand" Gate, monitors U3 and when the conditions are met for the number 10 (binary) it sends a signal to U2 which in turn sends a high analog signal to the output node 500.

U5, 8-Input "Nand" Gate, monitors U3 for the count of 30 (binary). When this condition is met it sends a low analog signal to U2 to the output node 500 and correspondingly resets U3.

Resistors R3 and R4 reduce the current at the inputs of the U2 and U6, Hex Buffers. U6 inverts signals to the desired levels for the Nand gate logic chips.

The white circles at the outputs of the CMOS chips represent an open connection.

The preferred embodiment of the present invention may be characterized in terms of the outline information in Table 6 which appears below.

TABLE 6 SALIENT FEATURES OF THE FIG. 1-5 APPARATUS

Intermittent circuitry 10-seconds ON/20-second OFF cycle. Operates intermittently or continuously on all power sources Operates on 115 VAC/(50–400 Hz), 1 A; 230 VAC/50 Hz, 1 A; 28 VDC, 6.5 A; and 12 V internal gel cell battery.

Back Panel mounted 115/230 VAC switch for transition from U.S. to overseas power sources Continuous charging of the internal battery while connected to any line power source Circuit breaker and fuse protection for both VAC and VDC input Automatic change to internal battery power from line power to provide continuous, uninterruptable operation 1-hour internal battery operation Cords for VAC and VDC sources Front Panel Switches On/Off
Intermittent/Continuous
VAC/VDC with protective cover
LED indicators: visible from a distance of 30 feet in subdued light;
Power
Battery Charge
Internal Battery
Low Battery
Physical Data;
Height: 8.25 inches
Width: 14.25 inches
Depth: 10 inches
Weight: 30.75 pounds
One bracket on each side for-1200 cc collection canister, Suction adjust; 0–570 mmHg Vacuum gauge (mmHg)-vacuum accuracy ±1% from set rate
Motor Rubber feet mounts for sound and vibration attenuation
Housing Rubber feet mounts to dampen transmitted vibration and prevent "walking"
Circuit board hinged to allow easy access for maintenance
Fine Screen shielded air vents on the side and bottom of the apparatus for ventilation and reduced EMI
Apparatus can aspirate fluid obstruction from patient airway, oropharyngeal or tracheal regions
Apparatus can remove blood or secretions from the stomach, or fluid or air from the thoracic cavity through a chest tube.
Apparatus can be used with standard chest drainage collection system
Uses standard sized suction tubing
Does not vent harmful gaseous vapors
Apparatus can operate without internal battery in place
Apparatus has securing bracket mounted to the back of housing for securing to pole
Capable of tie-down when sturdy securing is needed
Handle positioned to match the center of gravity of the apparatus
Several alternate arrangements of the invention are possible. Included in these changes are the items listed in Table 7 below.

TABLE 7, ALTERNATIVE ARRANGEMENTS

Plastic case for final product
Weight reduction results
Regulated Power Supply for AC line power
Weight reduction, if transformer omitted
Increased power efficiency, reduction of AC ripple
Increased efficiency and control of battery charging
A definite advantage if 115 VAC/400 Hz power input is not a requirement
Externally adjustable intermittent timer to control cycle time
12 VDC power input for ground vehicle and civilian vehicle use
Diaphragm suction pressure regulator-non flow rate sensitive
Automatic sensing and selection of applied electrical energy, DC, AC and voltage
Addition of filter between suction canister and vacuum inlet port—to prevent liquid transfer into suction pump.

The suction apparatus of the present invention therefore provides a portable source of medical suction that may be used with an individual patient and in fact accompany the patient during a plurality of transportation stages to a permanent medical facility and may be energized from most commonly available energy sources in transportation, temporary and permanent medical facilities. The apparatus has demonstrated an ability to withdraw 1200 millimeters of fluid in a time of ten seconds and performs successfully in the presence of large blood clots of up to 4 centimeters circumference without requiring special attention. The provided intermittent time cycle although fixed in duty cycle is typical of a time setting used in chest drainage or deep wound drainage. Although intended for use in the Military medical evacuation field the apparatus is readily adapted to use in civilian ambulance and air ambulance evacuation situation or use wherever a permanent suction utility is absent.

While the apparatus and method herein described constitute a preferred embodiment of the invention, it is to be understood that the invention is not limited to this precise form of apparatus or method and that changes may be made therein without departing from the scope of the invention which is defined in the appended claims

We claim:

1. Individual patient assignable portable medical suction generating apparatus comprising the combination of:

a low voltage direct current electrical energy operable suction pump member received in a hand carriable and patent litter apparatus mountable housing member;

a manually adjustable suction pressure controlling member shunt connected to a suction conduit member joining a suction inlet port of said suction pump member and a suction communicating port of said apparatus;

a rechargeable electrical battery member physically received within said housing member and having a nominal low voltage terminal potential that is compatible with said suction pump member;

first electrical input port means for receiving externally sourced direct current electrical energy into said apparatus;

first means for converting direct current electrical energy received at said first electrical input port means to battery charging direct current energy and suction pump operating direct current energy of said battery member nominal low terminal voltage level;

second electrical input port means for receiving externally sourced alternating current electrical energy of predetermined differing voltage level and differing alternation frequency characteristics into said apparatus;

second means for converting alternating current electrical energy received at said second input port means to battery charging direct current electrical energy and suction pump operating direct current electrical energy of said battery member nominal low terminal voltage level;

switching means for selecting between electrical energy input from said electrical battery member, said first input port means and said second input port means in response to manual and predetermined automatic selection criteria for energizing said suction pump member;

electronic timing circuit means responsive to a manual election input for operating said suction pump member in either a predetermined cycle of energized and non energized operating events or a continuously energized operating event.

2. The apparatus of claim 1 wherein said housing member includes engagement means for temporarily mounting said apparatus on a vertically disposed litter stanchion of a medical transport aircraft.

3. The apparatus of claim 1 further including first disposable suction canister mounting means received on said housing member for collecting body fluids removed from a patient by said apparatus.

4. The apparatus of claim 3 further including a second of said disposable suction canister mounting means received on said housing member.

5. The apparatus of claim 3 further including a front panel portion of said housing member which includes:
   a suction pressure indicating gauge;
   a suction pressure valve member;
   signal lamps for: suction pump operation, charging of said electrical battery member, low output voltage of said electrical battery member, and operation from said electrical battery member;
   a master ON OFF switch;
   a predetermined cycle-continuously energized manual election switch; and
   input selection switch means for selecting between said first electrical input port means direct current electrical energy and said second electrical input port means alternating current electrical energy.

6. The apparatus of claim 1 wherein said electronic timing circuit means includes electronic circuits for generating a ten seconds "ON", 20 seconds "OFF" operating cycle of said apparatus.

7. The apparatus of claim 1 wherein said externally sourced direct current electrical energy has a nominal potential difference of twenty eight volts and wherein said electrical battery member has a nominal terminal potential that is less than said twenty eight volts.

8. The apparatus of claim 7 wherein said electrical battery member has a nominal terminal potential of twelve volts.

9. The apparatus of claim 7 wherein said first means for converting direct current electrical energy, includes a direct current to direct current converter apparatus having a switching regulator circuit.

10. The apparatus of claim 1 wherein said externally sourced alternating current energy includes a combination of a nominal voltage selected from the voltages of one hundred fifteen and two hundred thirty volts; and a nominal frequency selected from the frequencies of fifty, sixty, and four hundred Hertz.

11. The apparatus of claim 10 wherein said second means, for converting alternating current electrical energy, includes a step down transformer having a pair of one hundred fifteen volt primary windings connectable in series or parallel and a full wave rectifier circuit.

12. The apparatus of claim 1 wherein said manually adjustable suction pressure controlling member includes a manually positionable needle valve member and wherein said needle value member enables a control of suction pressures between zero and negative five hundred sixty millimeters of mercury.

13. The apparatus of claim 1 wherein said switching means includes voltage responsive circuit means for energizing said suction pump member from said electrical battery member in response to a decrease in voltage potential difference in a selected one of said externally sourced direct current electrical energy and said externally sourced alternating current electrical energy.

14. The apparatus of claim 1 wherein said suction pump member has an electrical rating of one tenth horsepower, twelve volts at eight amperes and said electrical battery member has a nominal rating of twelve volts and ten ampere-hours.

15. The apparatus of claim 1 further including electrical filtering means received is said housing member for suppressing radio frequency interference signals originating in said apparatus and vacuum flow mechanical filtering means for excluding solid and liquid substances from said suction pump member.

16. Portable self contained and external energized medical suction generating apparatus for individual patient assignment during battle field, short and long distance transportation vehicle and temporary hospitalization environment usage, said apparatus comprising the combination of:
   a hand carriable portable housing member having a center of gravity disposed handle member, vibration resistant elastic-frictional feet members and an aircraft patient litter vertical stanchion receptacle engagement member received thereon;
   a twelve volt direct current electrical energy operable suction pump member of five hundred sixty millimeters of mercury column suction capability received in said portable housing member;
   a twelve volt ten ampere hour gelled electrolyte rechargeable electrical battery member received in said portable housing member;
   a suction level measuring gauge of at least said five hundred sixty millimeters of mercury suction capacity received in a frontal panel portion of said housing;
   a suction level controlling manually operable value member also received in said frontal panel portion of said housing member;
   disposable suction canister mounting means received in a plurality of locations on said portable housing member;
   first electrical input energy conveying means communicating into said housing member for supplying externally sourced twenty eight volt direct current electrical energy from an aircraft receptacle source to said apparatus;
   DC to DC first electrical energy conversion means received in said housing member and including solid state electronic switching means for converting said twenty eight volt direct current electrical energy to twelve volt electrical energy;
   second electrical input energy conveying means communicating into said housing member for supplying externally sourced alternating current electrical energy of one of the potentials of one hundred fifteen and two hundred thirty volts and one of the alternation frequencies of fifty, sixty and four hundred Hertz;
   AC to DC second electrical energy conversion means received in said housing member and including a dual voltage primary winding inclusive step down transformer member and a full wave bridge rectifier connected secondary winding for converting said alternating current electrical input energy to twelve volt electrical energy for charging said electrical battery member and energizing said suction pump member;
   manually operable electrical switching means received on said housing member frontal panel portion for selecting between said external direct current and alternating current electrical energy sources for charging said electrical battery member and energizing said suction pump member;

electrical switching means responsive to a selected electrical potential output of said first and second electrical energy conversion means for energizing said suction pump member from said electrical battery member upon failure of said selected electrical output from said receptacle sources;

electronic tinning circuit means received in said housing and responsive to a manual selection switch member received in said front panel portion for energizing said suction pump member in a ten seconds ON twenty seconds OFF operating cycle;

electrically energized visual illumination means received in said front panel portion for indicating to a human observer one or more operating events of:

present functioning of said suction pump member, a predetermined degree of discharge status of said electrical battery member, present energization of said suction pump member from said electrical battery member and ensuing recharge of said battery member;

circuit breaker means received in a back panel portion of said housing member for disconnecting said external direct current and alternating current electrical energy sources from said apparatus in response to current flow in excess of predetermined amplitudes therefrom;

radio frequency noise suppression means connected with said first and second electrical energy conversion means for limiting radio frequency spectrum noise emissions from said apparatus.

* * * * *